United States Patent [19]
Haglid

[11] Patent Number: 5,990,080
[45] Date of Patent: Nov. 23, 1999

[54] USE OF PROTEIN S-100-B IN MEDICINES CONTAINING THE PROTEIN S-100B

[75] Inventor: Kenneth G. Haglid, Hovås, Sweden

[73] Assignee: A+ Science Invest AB, Goteberg, Sweden

[21] Appl. No.: 09/051,589

[22] PCT Filed: Oct. 15, 1996

[86] PCT No.: PCT/SE96/01305

§ 371 Date: Apr. 15, 1998

§ 102(e) Date: Apr. 15, 1998

[87] PCT Pub. No.: WO97/14427

PCT Pub. Date: Oct. 15, 1996

[30] Foreign Application Priority Data

Oct. 17, 1995 [SE] Sweden .............................. 9503620-8

[51] Int. Cl.⁶ .......................... A10N 37/18; A61K 38/00; C07K 5/00; C07K 7/00

[52] U.S. Cl. ................. 514/2; 514/12; 530/300; 530/324; 424/400

[58] Field of Search .......................... 514/12, 2; 530/300, 530/324; 424/400

[56] References Cited

FOREIGN PATENT DOCUMENTS

| 9210200 | 6/1992 | WIPO | ............................ A61K 37/00 |
| WO92 10200 | 6/1992 | WIPO . | |

*Primary Examiner*—Avis M. Davenport
*Attorney, Agent, or Firm*—Burns, Doane, Swecker & Mathis, L.L.P.

[57] ABSTRACT

The present invention concerns the use of the protein S-100b in medicines for the stimulation of growth and survival of damaged neurons. The invention includes as well a medicine containing the S-100b protein in an aqueous solution which may contain also other biocompatible substances.

8 Claims, No Drawings

SEQUENCE LISTING

<160> NUMBER OF SEQ ID NOS: 1

<210> SEQ ID NO 1
<211> LENGTH: 92
<212> TYPE: PRT
<213> ORGANISM: Protein S-100b

<400> SEQUENCE: 1

```
Met Ser Glu Leu Glu Lys Ala Met Val Ala Leu Ile Asp Val Phe His
 1               5                  10                  15

Gln Tyr Ser Gly Arg Glu Gly Asp Lys His Lys Leu Lys Lys Ser Glu
                20                  25                  30

Leu Lys Glu Leu Ile Asn Asn Glu Leu Ser His Phe Leu Glu Glu Ile
            35                  40                  45

Lys Glu Gln Glu Val Val Asp Lys Val Met Glu Thr Leu Asp Glu Asp
        50                  55                  60

Gly Asp Gly Glu Cys Asp Phe Gln Glu Phe Met Ala Phe Val Ser Met
 65                  70                  75                  80

Val Thr Thr Ala Cys His Glu Phe Phe Glu His Glu
                85                  90
```

USE OF PROTEIN S-100-B IN MEDICINES CONTAINING THE PROTEIN S-100B

AREA OF THE INVENTION

The present invention concerns the use of a protein S100-b in medicines which aim at stimulating the growth of as well as survival of damaged neurons by primarily the administration of a medicine containing this protein via infusion or injection locally to the damaged region.

BACKGROUND OF THE INVENTION

Structure of Normal Peripheral Nerves. Kranial Nerves, Spinal Cord and Rhombencephalon Peripheral nerves and cranial nerves as well as the spinal cord constitute a functional unit which is responsible for the movements of the body. The unit includes also sensory impulses to the cerebrum and the cerebellum. When undamaged, the unit provides information directed inwards and outwards which is a prerequisite for our daily life.

Each neuron consists of a cell body (perikaryon or soma) as well as two types of processes, one which receives information (dendrites) and one which delivers information (axon) as electrical impulses. The axons of peripheral nerves and cranial nerves are contained within Schwann cells which produce myelin, an insulating lipid-rich material which isolates each axon from the others. In the spinal cord and the rhombencephalon, oligodendroglial cells surround the axons and form the myelin sheaths. In addition, other cell types, such as astrocytes and microglial cells, are present in the spinal cord.

Astrocytes make up 50–70% of the volume occupied by glial cells in the brain. They maintain the microenvironment of the neurons. The microglial cells are much fewer. They are activated during damage to the brain and phagocytize dead material. Furthermore, they play a key role in the immune system of the brain.

Organization of the Peripheral Nerves and the Spinal Cord

The peripheral nerves are made up of axons which mediate impulses to the muscles which in turn cause contractions (motor axons) and axons which mediate information from muscle spindles, tendons joint capsules and the skin (sensory axons). The motor axons are the processes from large perikarya localized in the anterior horns of the spinal cord. The sensory axons have their perikarya in the dorsal root ganglia where they are surrounded by satellite glial cells. The sensory neurons in the spinal cord transfer the information further to the cerebellum and cerebrum.

Structure of the Spinal Cord

The neuronal perikarya of the spinal cord are organized as grey matter which, in the cross section, is shaped like an H. This is surrounded by white matter which contains axons travelling up or down.

Structure of Rhombencephalon and the Cranial Nerves

Ten out of the twelve cranial nerves have their perikarya located in groups (nuclei) within the rhombencephalon. The cranial nerves have either a motor or a sensory function.

REACTION TO DAMAGE

Inflammation and Cellular Response to Damage

Damage to brain tissue leads to an inflammatory response which is characterized by a vascular response as well as a cellular response, both aiming at defending the body against foreign substances and to dispose of dead and dying tissue. The inflammation per se also prepares the tissue for the process of repair. If axons are sewered, their peripheral parts consistently degenerate. The proximal portions of certain axons, as well as their perikarya degenerate as well and die.

The magnitude of the inflammatory and degenerative processes depends on the size of the damage, the condition of the tissue, as well as on the capacity of the body to provide a response. The primary sign of initiation of the repair process is the growth of axons from surviving perikarya and the elongation of surviving proximal portions of axons. These axons grow through the damaged region and into the sheaths of the degenerated distal part of the nerve or into the spinal cord. This process is slow (a few millimeters per day) and the result of it is uncertain, since the target organs (muscles, blood vessels, skin, tendons, joints, cartilage, bone) which have not received nerve pulses for some time, tend to degenerate prior to the arrival of the growing axons. This leads to a reduced muscle power or paralysis as well as reduced sensory information which indeed constitutes a severe handicap for the affected individual. This type of damage is a considerable socioeconomic drawback also for the society.

Cellular Phases of Nerve Tissue Repair

Two principal types of damage may appear. The first is due to compression of the nerve tissue (axon), while its myelin sheath (basal membranes, endo, peri and epineurium) which surrounds the dying axon remains intact. The second type is due to a loss of nerve tissue, in which case there is a gap between the proximal part and peripheral part of the axon. Repair of this type of nerve damage requires bridging constructs (silicon chambers, transplants of nerves or other tissues). The cellular response is similar in the two types of damage. The degenerating tissue is first invaded by macrophages which initially remove damaged components and dying material. The damaged region is invaded by fibroblasts and small blood vessels within a few days. The Schwann cells then grow and invade the damaged region from the proximal end of the nerve. Then axons from the surviving perikarya grow in close association with the Schwann cells.

A considerable amount of knowledge has accumulated during the last few decades concerning the mechanisms which regulate the activity of the cells during the process of repair. Chemotactic peptides have been isolated and the role of prostaglandins and related compounds is partly clarified. The details of the steps in the processes which lead to improved repair and regeneration are, however, largely unknown.

EVALUATION OF PRESENTLY EMPLOYED METHODS FOR THE REPAIR OF DAMAGE AND THEIR LIMITATIONS

Peripheral Nerves

A number of different techniques are employed for the repair of damage on peripheral nerves and cranial nerves. In the case of a clearcut sewering, the nerve stumps are connected by suturing. There are more problems when part of the nerve is lost. The presence of granulation tissue and collagen usually prevent a functional tissue repair process. This is largely due to a deficit of axons which can bridge over to the peripheral part of the nerve, i.e. that which leads to the target organs.

When part of the nerve is missing, a transplant has to be sutured to bridge the proximal with the peripheral nerve stumps. A silicon tubing or a nerve transplant is mostly employed. Presently tests are performed with muscle transplants which have been made acellular by repeated freezing and thawing (liquid nitrogen—room temperature). However, the results are still fairly poor.

The degree of growth of axons and Schwann cells may be stimulated by the administration of growth factors.

CONCLUSION

In the case of a large damage to peripheral nerves, cranial nerves or the spinal cord, the regeneration capacity is poor or absent and the result of the repair process is a reduced functional capacity. Small nerve damages, on the other hand, cause usually negligible defects. Consequently, there is a considerable need for improvement of the repair process after large damages. Such improvements may also be helpful for the repair of minor damage.

A number of factors which promote or reduce the rate of tissue repair have been described during the last decade. Many of these derive from tumors or are associated with tumors (oncogenes). Some of these products stimulate growth, either in an unspecific fashion or directed to a specific type of tissue or organ. A considerable problem is that some of these compounds may induce transformations and/or have unwished side-effects.

Criteria for a Neurotrophic Factor

A neurotrophic factor stimulates growth of nervous tissue. The following criteria has to be fulfilled by a substance in order to classify it as a neurotrophic factor (NTF).
1. A neuron which employs NTF should contain NTF and have receptors for NTF.
2. The neuron should survive in the presence of NTF and die in its absence.
3. A machinery for the synthesis of NTF should be present in the target cells or in other cells in contact with the neuron.
4. NTF should support the elongation of those processes which take place in those specific groups of cells which fulfil criterium 1.

S-100b as a Neurotrophic Factor

The S-100 family, i.e. S-100a, S100b, S-100L, S-100G, calpactin LC, calcylin and calbindin9K are small, acid, calcium-binding proteins which probably are involved in the progression of the cell cycle, in cell differentiation and in the interactions between the cytoskeleton and the plasma membrane of the cell. The "original" S-100 molecule was discovered 30 years ago and was given its name due to its solubility in 100% ammonium sulphate. S-100 has three dimeric isoforms, S-100a0, S-100a and S-100ab, which are formed by $\alpha\alpha$, $\alpha\beta$ and $\beta\beta$ subunits. S-100b dominates quantitatively in mammalian brains and is the only component in the rat brain.

The presence or not of S-100 in neurons is a controversial question since 20 years. One reason is that tissue fixation with aldehydes tends to mask the antigenic properties of S-100b. In my research, I have recently ascertained the presence of S-100b in certain populations of neurons in the rhombencephalon of the rat. In this discovery, I have employed a new method for the expression of the S-100b antigen (Yang, Q Hamberger, A. Hyden, H. Wang, S. Stigbrand, T and Haglid, K. G., S-100b has a neuronal localization in the rat hindbrain revealed by an antigen retrieval method, Brain Res., 696 (1995) 49 61.)

The S-100 immunoreactivity of neurons in the developing brains of, in particular rodents, was generally overlooked in previous work, largely due to the choice in those studies of brain regions and/or of stages of development of the animal.

Only part of the neuronal population contains S-100b or has receptors for S 100b. I have described above a method which has the capacity to determine which neurons contain the protein or its receptors. I have shown that, in the rat, the presence of S-100b increases postnatally in certain neurons and that a large number of these neurons contains S-100b or has receptors for S-100b on their surface. In the adult rat, the S-100b containing neurons are found in the mesencephalon, namely in the red nucleus, the oculomotor nucleus, the mesencephalic trigeminal nucleus, in the pons, namely the pontine reticular nucleus: -oral, -caudal, -ventral, and the motor trigeminal nucleus, in the medulla oblongata, namely in the facial nucleus, the vestibular and lateral vestibular nuclei, in the cerebellum, namely in the cerebellar nuclei, in the spinal cord, namely in the motor neurons and, finally, in the sensory neurons of the dorsal root ganglia. These groups of neurons represent examples of neurons which may be influenced by the medicine according to the present discovery. In addition, other neurons may be influenced by the medicine.

The Problem

Neurological expertise has estimated that a large number of damages to peripheral nerves, cranial nerves and the spinal cord heal incompletely, i.e. the target organs degenerate or undergo fibrotic changes. Such complications give frequently functional handicaps as well as social disturbancies and reduced working capacity. One of the most important goals of biomedical research is, since many years, an improved and more rapid healing of damage to the nervous system.

The Solution

According to the present invention, the mentioned problem is considerably reduced, since the use of the S-100b protein in medicines stimulates the growth of nerves and promotes the survival of damaged neurons.

According to the invention, the S-100b protein is useful for neurons which have receptors for S-100b and/or contain S-100b.

The invention concerns also the use of the S-100b protein for neurons which have been damaged by diseases such as amytrofic lateral sclerosis and multiple sclerosis.

The invention concerns also a medicine which contains the S-100b protein for stimulation of nerve growth and the survival of damaged neurons.

According to the invention, the medicine may contain S-100b in a concentration of 0.1 to 1000 $\mu$g/ml in a water solution which may contain also other biocompatible substances.

According to the invention, the medicine shall be administered by infusion or injection with e.g. a mini-osmotic pump to the damaged region.

There are no indications that S-100b has oncogenic or oncogen-related properties. S-100b is an endogenous peptide which may be produced with known biotechnological methods. S-100b has a strictly local effect and has hardly any side effects after local administration.

S-100b is, as mentioned above, a peptide with the following amino acid sequence of the monomer subunit ($\beta$):

Met Ser Glu Leu Glu Lys Ala Met Val Ala Leu. Ile Asp Val Phe His Gln Tyr Ser Gly Arg Glu Gly Asp Lys His Lys Leu Lys Lys Ser Glu Leu Lys Glu Leu Ile Asn Asn Glu Leu Ser His Phe Leu Glu Glu Ile Lys Glu Gln Glu Val Val Asp Lys Val Met Glu Thr Leu Asp Glu Asp Gly AspGly Glu Cys Asp Phe Gln Glu Phe Met Ala Phe Val Ser Met Val Thr Thr Ala Cys His Glu Phe Phe Glu His Glu

Consequently, S-100b reduces the time required for nerve regeneration. This reduces, in turn, the functional and social incapacity of the patient, since the rehabilitation period after a major nerve damage is shortened. This reduces problems arising from muscle inactivity and changes in the structure of bones and other organs. The dose of S-100 which is required, varies within a wide range and is determined by the type, degree and localization of the damaged tissue. Treatment is required for days or weeks.

Examples of the use of S-100b and medicines containing S-100b for local administration to rats in which the sciatic nerve previously had been damaged and a piece of it removed, are given below.

EXAMPLES

1. S-100b was used at a concentration of 0.5–1000 μg/ml in a salt solution which was buffered with 100 mM phosphate, had a pH of 7.2 and contained 2.5 mM CaCl$_2$ as well.
2. S-100b was used at a concentration of 0.1–1000 μg/ml in 1% bovine serum albumin (BSA) in a buffered salt solution which also contained 2.5 mM CaCl$_2$.
3. S-100b was used at a concentration of 0.5–1000 μg/ml in a salt solution which also contained 2.5 mM CaCl$_2$.
4. S-100b was administered in a gel made of hydroxy-methyl-cellulose at a concentration of 25 μg/ml (made by Apoteksbolaget AB, Umeå, Sweden).
5. S-100b was dissolved in a gel made of hydroxy-methyl-cellulose at a concentration of 10 μg/ml.
6. S-100b was dissolved to a concentration of 2.5 μg/ml in a gel made of 3% hydroxy-methyl-cellulose.
7. S-100b was administered with an osmotic minipump in a concentration of 0.5–10 μg/ml to the region of a damaged sciatic nerve in rats. A 10 mm portion of the sciatic nerve was removed and replaced by an acellular (frozen-thawed) muscle transplant which bridged the proximal and the distal nerve stumps. Twelve rats were used as controls and to these the solution without S 100b was administered. Eleven rats were given S-100b (0,57 μg/h) for 6 days with an Alzets osmotic minipump. The length of nerve regeneration into the acellular transplant was determined on the sixth day with a pinch test. The results are shown below.

| Mann-Whitney U for pinch Grouping Variable: grupp | |
|---|---|
| U | 11.000 |
| U Prime | 121.000 |
| Z-Value | −3.385 |
| P-Value | .0007 |
| Tied Z-Value | −3.391 |
| Tied P-Value | .0007 |

| # Ties | 4 | | |
|---|---|---|---|
| Mann-Whitney Rank info for pinch Grouping Variable: grupp | | | |
|  | Count | Sum Ranks | Mean Rank |
| ha | 11 | 187.000 | 17.000 |
| kontroll | 12 | 89.000 | 7.417 |

The "MeanRank" value of 17.000 was calculated for the rats which had been treated with S-100b (lower right of the table) while the corresponding controls had the value of 7.417. The ratio of these two numbers shows that the axons which had been treated with the medicine according to the present discovery had grown 2.3 times more than the unstimulated control axons. The probability test of the significance of this difference gave a P-value of less than 0.0007.

Consequently, medicines which contain S-100b improves the regeneration and repair as well as survival of different types of nerve tissue. Accordingly, not only the growth of the axons is stimulated but the treatment also increases the capacity for survival of the neurons.

The invention is not limited to the examples given above but can be varied in different ways within the frame of the patent claims.

---

---

What is claimed is:

1. A method for stimulating the growth or survival of neurons which comprise S-100b or which comprise a receptor for S-100b in a subject in need of such treatment, comprising administering an amount of a S-100b protein effective to stimulate or promote the survival of said neurons.

2. The method of claim 1, wherein said treatment is to promote the growth or survival of neurons damaged by a disease selected from the group consisting of amyotrophic lateral sclerosis or multiple sclerosis.

3. The method of claim 1, wherein said neurons are selected from the group consisting of neurons comprised in the mesencephalon, neurons comprised in the red nucleus, neurons comprised in the oculomotor nucleus, neurons comprised in the mesencephalic trigeminal nucleus, neurons comprised in the pons, neurons comprised in the pontine reticular nucleus; neurons comprised in the motor trigeminal nucleus, neurons comprised in the medulla oblongata, neurons comprised in the facial nucleus, neurons comprised in the vestibular and the lateral vestibular nuclei, neurons comprised in the cerebellum, neurons comprised in the cerebellar nuclei, neurons comprised in the spinal cord, neurons comprised in the motor neurons, and sensory neurons of the dorsal root ganglia.

4. The method of claim 1, wherein said S-100b protein is administered in the form of a composition comprising a concentration of said protein ranging from 0.1 to 100 μg/ml in an aqueous solution.

5. The method of claim 4, wherein said solution further comprises other biocompatible substances.

6. The method of claim 1, wherein said S-100b protein is administered by infusion or injected into an area comprising damaged neurons.

7. The method of claim 6, wherein said administration is effected using an osmotic mini pump.

8. The method of claim 1, wherein said treatment is effect for a period of days or weeks.

* * * * *